US009272281B2

(12) United States Patent
Richter et al.

(10) Patent No.: US 9,272,281 B2
(45) Date of Patent: Mar. 1, 2016

(54) METHOD AND DEVICE FOR TARGETED PROCESS CONTROL IN A MICROFLUIDIC PROCESSOR HAVING INTEGRATED ACTIVE ELEMENTS

(71) Applicant: Technische Universität Dresden, Dresden (DE)

(72) Inventors: Andreas Richter, Dresden (DE); Rinaldo Greiner, Dresden (DE); Merle Allerdissen, Dresden (DE)

(73) Assignee: Technische Universität Dresden, Dresden (DE)

( * ) Notice: Subject to any disclaimer, the term of this patent is extended or adjusted under 35 U.S.C. 154(b) by 35 days.

(21) Appl. No.: 14/387,315

(22) PCT Filed: Apr. 11, 2013

(86) PCT No.: PCT/EP2013/057631

§ 371 (c)(1),
(2) Date: Sep. 23, 2014

(87) PCT Pub. No.: WO2013/153181

PCT Pub. Date: Oct. 17, 2013

(65) Prior Publication Data

US 2015/0044688 A1 Feb. 12, 2015

(30) Foreign Application Priority Data

Apr. 13, 2012 (DE) ........................ 10 2012 206 042

(51) Int. Cl.
*G01N 15/06* (2006.01)
*G01N 33/00* (2006.01)
(Continued)

(52) U.S. Cl.
CPC ... *B01L 3/502738* (2013.01); *B01L 2200/0621* (2013.01); *B01L 2300/04* (2013.01);
(Continued)

(58) Field of Classification Search
CPC ........ G01N 15/06; G01N 33/00; G01N 33/48
USPC ............... 422/50, 502, 503, 504; 436/43, 180
See application file for complete search history.

(56) References Cited

U.S. PATENT DOCUMENTS 5,798,215 A * 8/1998 Cathey et al. .................. 435/7.9
5,846,396 A * 12/1998 Zanzucchi et al. .............. 506/33
(Continued)

FOREIGN PATENT DOCUMENTS

DE 102006051535 A1 12/2008
WO 2011157735 A2 12/2011

OTHER PUBLICATIONS

Viets, John; Deen, William; Troy, Julia; Brenner, Barry: "Determination of Serum Protein Concentration in Nanoliter Blood Samples Using Fluorescamine or o-Phthalaldehyde", Analytical Biochemistry 88, 513-521 (1978).
(Continued)

*Primary Examiner* — Brian J Sines
(74) *Attorney, Agent, or Firm* — Michael Soderman

(57) ABSTRACT

The invention relates to a microfluidic micromechanical system having integrated active elements (7) and a method for microfluidic process control in a microfluidic micromechanical system. According to the invention, the microfluidic system comprises integrated active elements (7), which can be activated without auxiliary energy by means of ambient variables that can be influenced and which are designed to bring about active functions as a result of the change of the swelling state thereof or the mechanical properties thereof. The microfluidic micromechanical system further comprises at least one structural support (2) having at least one first (3) and one second (4) channel, wherein a reaction chamber (6) bounded by active elements (7) is formed in an overlapping region (5) of the first and second channels.

12 Claims, 11 Drawing Sheets

(51) Int. Cl.
*G01N 33/48* (2006.01)
*B01L 3/00* (2006.01)

(52) U.S. Cl.
CPC .. *B01L2300/0816* (2013.01); *B01L 2300/0864* (2013.01); *B01L 2300/0867* (2013.01); *B01L 2300/0874* (2013.01); *B01L 2400/0672* (2013.01); *B01L 2400/0677* (2013.01); *Y10T 436/2575* (2015.01)

(56) References Cited

U.S. PATENT DOCUMENTS

| | | | | |
|---|---|---|---|---|
| 6,030,580 | A * | 2/2000 | Raasch et al. | 422/40 |
| 8,062,611 | B2 * | 11/2011 | Faulstich et al. | 422/537 |
| 2005/0250200 | A1 | 11/2005 | Nakajima et al. | |
| 2006/0169339 | A1 | 8/2006 | Oh | |
| 2008/0069729 | A1 | 3/2008 | McNeely | |
| 2010/0240022 | A1 | 9/2010 | McNeely | |
| 2011/0126913 | A1 | 6/2011 | Banerjee | |

OTHER PUBLICATIONS

Ci, Yun-Xiang; Chen, Lie: "Fluorimetric Determination of Human Serum Albumin with Eriochrome Cyanine R", Analyst, Apr. 1988, vol. 113.

Dongshin Kim et al: "Hydrogel-Based Reconfigurable Components for Microfluidic Devices", Lab on a Chip, vol. 7, No. 2, Feb. 1, 2007, pp. 193-198, XP055069263, ISSN: 1473-019, DOI: 10.1039/b612995a The whole document.

Wang, J.; Chen, Z.; Mauk, M; Hong, K-S; Li, M; Yang, S; and BAU, H; 2005, "Self-Actuated, Thermo-Responsive Hydrogel Valves for Lab on a Chip", Biomedical Microdevices 7 (4), 313-322.

Pal, Rohit; Yang, Ming; Johnson, Brian; Burke, David; Burns, Mark: "Phase Change Microvalve for Integrated Devices", Anal. Chem. 2004, 76, 3740-3748.

Duffy, David; McDonald, J.; Schueller, Olivier; Whitesides, George: "Rapid Prototyping of Microfluidic Systems in Poly(dimethylsiloxane)", Anal. Chem. 1998, 70, 4974-4984.

Richter, Andreas; Paschew, Georgi: "Optoelectrothermic Control of Highly Integrated Polymer-Based MEMS Aplied in an Artificial Skin", Adv. Mater. 2009, 21, 979-983, Wiley-VCH Verlag GmbH & Co. KGaA, Weinheim, Germany, www.advmat.de.

* cited by examiner

METHOD AND DEVICE FOR TARGETED PROCESS CONTROL IN A MICROFLUIDIC PROCESSOR HAVING INTEGRATED ACTIVE ELEMENTS

CROSS REFERENCE TO RELATED APPLICATIONS

This application is the U.S. national stage of International Application No. PCT/EP2013/057631 filed on Apr. 11, 2013, and claims the benefit thereof. The international application claims the benefit under 35 USC 119 of German Application No. DE 102012206042.1 filed on Apr. 13, 2012; all applications are incorporated by reference herein in their entirety.

BACKGROUND OF THE INVENTION

The invention relates to a microfluidic, micro-chemomechanical system with integrated active elements and a method for microfluidic process control in a microfluidic, micro-chemomechanical system.

Microfluidic processors are primarily used today in biological, biochemical and chemical processes; above all their use as "labs on chips" (LOC), "chip laboratories" or "micro-total-analysis systems" (μTAS) is at the focus of scientific developments.

The LOC concept offers diverse advantages. The reduction of fluid volumes makes the analysis of very small sample quantities possible and thrifty use of reagents and samples that are frequently valuable, rare, harmful or dangerous. Higher throughputs are also achievable in that way, because shorter provision, mixing and reaction times are required with minimized energy consumption due to the smaller quantities. The process control can also be relieved of some of its burden because of shorter system response times.

Overall, LOC structures make significant process streamlining possible by considerably reducing the processing time and therefore increasing the possible throughput, as well as reducing the quantities of required resources (test subjects, analytes, reagents and auxiliary resources).

PRIOR ART

Microfluidic systems with active elements are known in the prior art.

Active fluidic elements based on solid-state actuators such as piezoelectric actuators (U.S. Pat. No. 5,224,843 and U.S. 2003/0143122) and shape-memory actuators (U.S. Pat. No. 5,659,171) are described. They are, in fact, easy to miniaturize as individual elements, but they have a complicated structure, are tied to certain materials that are mostly not plastic-based and have to therefore be manufactured separately. Possible hybrid integration (e.g. gluing the elements onto the LOC) is not economical as a rule.

Conversion elements based on changes in the aggregate state can be integrated with a slight amount of intervention in part in the layout of the channel-structure support and are therefore usually compatible with the manufacturing process for the molded plastic parts of the channel-structure support. Melting elements (R. Pal et al., Anal. Chem. 16 (2004) 13, pp. 3740-3748) and freezing elements (U.S. Pat. No. 6,536,476) and thermal bubble generators (U.S. Pat. No. 6,283,718) are known, for example.

DE 101 57 317 A1 discloses a basic element of a microfluidic processor that is compatible with electronics through an electrically or electronically controllable interface quantity via the control of the degree of swelling of polymer networks capable of swelling with volume-phase transition behaviors, especially hydrogels. Physical quantities that can be simply generated via electronic or electrical means and that trigger volume-phase transitions in polymer networks capable of swelling preferably serve as controllable environmental variables or interface quantities in the process. A very simple control quantity that can be electrically created is the temperature.

The drawback of these hydrogel-based active elements is above all the necessity of using electrically generatable control quantities to create the volume-phase transitions; the operation of microfluidic systems of that type is inescapably tied to electrical components because of that. A self-sufficient use of microfluidic systems is ruled out because of that.

WO 2008/049413 discloses a microfluidic system with active elements that can be controlled without auxiliary energy. Above all hydrogel-based active elements are disclosed here that make a volume-phase transition possible in dependence upon temperature or solvent. In the process, the active elements bring about an active function via a change in the degree of swelling or the mechanical properties. Moreover, swelling-medium barriers are disclosed that swell because of the absorption of solvent and, as a result, bring about a limitation of the swelling-medium supply.

The use of active elements free of auxiliary energy allows a largely self-sufficient use of microfluidic systems, especially in diagnostics; the establishment of one-time analysis systems would be favored by not using external electrical energy sources and the use of chemical energy sources.

Further development of microfluidic, micro-chemomechanical systems would therefore be very desirable.

DETAILED DESCRIPTION

The object of this invention is therefore to specify a microfluidic, micro-chemomechanical system that has active elements operated without auxiliary energy and is capable of carrying out volumetrically defined mixture reactions over defined time sequences.

Description of the Invention

The problem is solved by a microfluidic, micro-chemomechanical system in accordance with claim 1. Advantageous design forms are specified in the dependent claims.

Advantageous design forms are specified in the dependent claims.

As per the invention, the microfluidic system comprises integrated active elements designed to be activated, free of auxiliary energy, by influenceable environmental variables and to bring about active functions via a change in their swelling state or their mechanical properties. The microfluidic, micro-chemomechanical system is comprised here of at least one structure support with at least one first channel that belongs as a rule to a first channel system with a first process medium. Furthermore, it includes at least one cover that at least partially covers the structure support, as well as at least one second channel of a second channel system that is either integrated onto the structure support, which already supports the first channel of a first channel system, or is integrated into the cover. The first and second channels have reservoir chambers in a joint overlay area. The reservoir chambers are limited by active elements and are able to form a joint reaction chamber.

"Free of auxiliary energy" in the sense of this invention is understood to mean doing without the supply of energy from an external electrical or thermal energy source to the active elements as per the invention. Microfluidic elements are known in the prior art that can be activated by electrical and thermal energy; hydrogels that can be switched in a thermal or electrical fashion can be mentioned here as examples.

An overlay area is understood in the sense of this invention to mean the part between two reservoir chambers that can be connected and that have a common wall. The mixing of the first and second liquids that flow into the reaction chamber takes place in this mixture zone.

An active element or an active function is understood here to mean an active mechanical element or an active mechanical function, respectively.

The cover is designed to be an upper structure support in an arrangement of at least two structure supports in one embodiment of the invention.

In one embodiment of the invention, a membrane is arranged between the first and second channels in the overlay area of the first and second channel systems; the joint reaction chamber is divided up into a first reservoir chamber and a second reservoir chamber because of that. A separation of the liquids in the first and second channels is brought about because of that, which is why an undesired displacement of liquids, e.g. as a result of a delayed flow of a liquid, is prevented in one of the two channels. The second liquid could enter into the first channel via the joint reaction chamber because of a slowdown in the flow, especially as a result of a blockage, which is why an undefined mixture of the first and second liquids would take place, not as desired in the joint reaction chamber, but instead already in the first channel. As a consequence, the volumetrically undefined mixtures that are created in this way would be unsatisfactory for analysis purposes. An undesired displacement of the liquids into the other respective reservoir chamber is prevented by the separation of the two liquids by means of a membrane.

The membrane is designed to be an active membrane in a further embodiment.

In another embodiment of the invention, the membrane between the first and second reaction chambers is made of a liquid-soluble material. The membrane can be dissolved after the first and second reservoir chambers are filled with the two liquids because of that, which is why the reservoir chambers are connected to form the joint reaction chamber and the liquids can be mixed in it as intended. This advantageously takes place when the other active elements, which limit the reaction chamber and which are designed to be swelling-medium barriers with swelling capabilities, prevent a subsequent flow of liquids from the channels into the reaction chamber. A hermetically sealed reaction chamber is realized because of the swelling of the swelling-medium barriers that distinguishes itself by defined liquid volumes in the reservoir chambers in each case, which are then connected to one another by the later dissolution of the membrane so that their contents can be mixed with each another. In the process, the membrane can be configured in accordance with the needs of the application in such a way that the time-related course of the dissolution makes a mixture of the liquids in the reaction chamber possible at the desired point in time. The time-related dissolution behavior of the membrane when it is in contact with a liquid can be adjusted in terms of the design by both the selection of the material and the thickness of the membrane. This is especially advantageous, because an undefined displacement of the liquids can thereby be avoided when slowdowns in the flow arise in one of the two channels and a slowed-down flow into the reaction chamber associated with that. More than two channel systems could, of course, also be connected to one another as described to carry out mixing processes with more than two liquids.

In a further embodiment of the invention, the active element is designed to be a delivery system of active ingredients and the ingredients in the base area of the second reservoir chamber of the reaction chamber. In so doing, active ingredients and/or other substances can be embedded or fixed in place in the active element; these active ingredients and/or other substances are released by the activating environmental variable. Active ingredients and/or other substances such as enzymes, substrates, precursors etc. can be immobilized in advance in the reaction chamber because of that and mobilized when a liquid is present; the time-related release of the active ingredients and/or other substances can be adapted in turn to the needs of the user. As an example, a release is possible after activation of the active elements limiting the reaction chamber, so the active ingredients and/or other substances will be released into the volume defined by the reaction chamber. It is also conceivable for the release to take place even before the dissolution of the membrane. In the first case, a mixture of the first and second liquids would come about in the reaction chamber; the second liquid would already contain the active ingredients and/or other substances. Applications of this type would be conceivable for targeted immobilizations of various substrate concentrations in different reaction chambers, for instance. In the other case, the release into the reaction chamber would only take place after the mixture of the first and second liquids. That would be advantageous if the first and second liquids are supposed to first carry out a reaction and the addition of a substrate etc. is only possible after the conclusion of this reaction. A broad range of possibilities for use of the microfluidic, micro-mechanical system opens up in the analysis because of the targeted immobilization of the active ingredients and/or other substances. The delivery system of active ingredients and other substances is designed to be a storage area or storage unit, for instance, that is activated by the presence of liquid. It can therefore absolutely be called an active element. A storage element of that type could also be designed to be a polymer network. It releases the swelling agent and the substances contained in it during the de-swelling process or dissolution process caused by the presence of a liquid.

In a further embodiment of the invention, the active elements are designed to be capable of being activated by the presence of liquid as an environmental variable. In so doing, both a change in the swelling state via the absorption of liquid and a dissolution of the active element as a result of the contact with liquid are conceivable.

In a further embodiment of the invention, the active elements are designed to specify the time-related sequence and the time-related behavior of the mixture of the first and second liquids. The time-related behavior of the mixture of the first and second liquids can be directly influenced by the variation of the structure of the active elements. In the process, the active elements can be controlled with regard to their time-related behavior via a suitable selection of materials. The time-related behavior can also be influenced by the dimensioning of the active elements. As an example, active elements with larger dimensions that experience an increase in volume because of the activating environmental variable can achieve a quicker stop to the flow of liquid than is the case for active elements with comparatively smaller dimensions. A slower dissolution as a result of a larger dimensioning of the active element can likewise also be set in a targeted way in the case of active elements that are soluble in liquid. The time-related sequence can be controlled both in dependence upon material and in dependence upon dimension because of that.

In a further embodiment of the invention, the active elements are designed to be swelling-medium barriers or liquid-soluble barriers. In the case that the active elements are designed to be swelling-medium barriers, the volume of the active element would increase via an absorption of liquid, which is why the channel that contains the active element narrows more and more until a breakdown in the flow in the channel, and consequently a stoppage of the flow, comes about as a consequence of a complete filling of the cross section of the channel. The active element that is designed to be a swelling-medium barrier is put in a dry state into the channel of the microfluidic, micro-mechanical system in the process. After the volume of the swelling-medium barrier has increased, the swelling-medium barrier remains in swollen state. This means that no de-swelling takes place after the increase in volume, which is why the swelling-medium barrier only experiences a one-time activation by the absorption of liquid. This is especially advantageous when the swelling-medium barrier is designed to be a closing element, for instance to block off the reaction chamber from subsequently flowing liquids.

When the active elements are designed to be a liquid-soluble barrier, a dissolution of this barrier is achieved when the barrier is wetted with the liquid in the channel. An increase in the flow of the channel cross section and, as a result, the development of a flow of the liquid through the channel come about with a progressive dissolution of the barrier because of that. The basis for regarding a dissolving element as an active element is established by its functional principle. The load-carrying capability or mechanical pliability of a component can be changed with a change (a) in the modulus of elasticity of the component material or (b) its cross section. In the case of a dissolving element, (b) is used as the basis for the active function. The dissolvable active element fulfills the function of an opening valve here as soon as the control signal "liquid" is applied.

In a further example of the invention, the swelling-medium barriers or liquid-soluble barriers are designed to be valves. The active elements can carry out valve functions in the microfluidic, micro-chemomechanical system because of the swelling or dissolution of the barriers that can be defined in terms of time. The valves can exercise both opening (liquid-soluble barrier) and closing functions (swelling-medium barriers) because of that. Valves of that type are suitable for use, as a preference, in autonomous microfluidic systems due to the exercise of functions in a chronologically definable fashion and without the use of auxiliary energy. In the process, all of the active components that fulfill the function of an opening valve are regarded as opening elements. This can take place via (a) a reduction in the modulus of elasticity in the case of cross-linked, swelling polymers and (b) a dissolution in the case of liquid-soluble materials. The dissolving membranes are likewise regarded as opening elements.

In a further embodiment of the invention, the active elements are comprised of hydrogels that are chemically cross-linked and/or physically interlaceable. Hydrogels in the sense of the invention are understood to mean a polymer containing water, but not water-soluble, whose molecules are chemically linked to form a three-dimensional network, e.g. via covalent bonds, or physically, e.g. via the interlacing of the polymer chains. They swell up in liquids with a considerable increase in volume, but without losing their material cohesion, because of built-in hydrophilic polymer components. What is essential here is that the hydrogels are designed in such a way that they remain in the swollen state after contact with liquids.

In a further embodiment of the invention, the active elements are made up of hydrogels that are selected from the group consisting, for instance, of polyacrylamides, polyvinyl alcohols, polyacrylates, hydroxycellulose, polyvinyl pyridines or polyglycols (e.g. polyethylene glycol, polypropylene glycol) and their derivatives.

In a further, alternative embodiment of the invention, the active elements are made of non-cross-linked polymers, salts or natural organic substances such as saccharides. This is the case when the active elements are designed to be liquid-soluble barriers. In so doing, all of the materials that form a solid, sol-gel or the like in the dry state and that dissolve when coming into contact with a liquid can be used. The material basis of the non-cross-linked polymers can be the same in principle as is the case with cross-linked polymers. Whereas the polymers that are cross-linked to form a three-dimensional network serve as swelling-medium barriers with swelling capabilities, the same polymers dissolve in the liquid when they are not cross-linked, because the polymer chains that are not connected to one another can be dissolved.

The subject matter of this invention is also a method for microfluidic process control in a microfluidic, micro-mechanical system; a first liquid is brought into a first channel, a second liquid is brought into a second channel, and the first and second liquids are mixed in a reaction chamber that is formed in the overlay area of the first and second channels, wherein the time-related sequence of the mixing of the first and second liquids in the reaction chamber is determined by active elements.

The process steps described above are advantageous, in particular, for the time-related control of the mixture of two liquids in a microfluidic system. The time-related sequence of process steps that are desired in each case, such as mixing, dissolving barriers, closing of desired channel sections by means of swelling-medium barriers and releasing active ingredients and/or other substances, can thereby be achieved in a user-specific way via the suitable choice of parameters.

In a further embodiment of the invention, the time-related sequence of the mixing of the first and second liquids in the reaction chamber is determined by the active elements that are designed to be liquid-soluble or a swelling-medium barrier. Both prevention of the flow and an opening of channel sections for a flow can be realized with the first or second liquid because of that.

In a further embodiment of the invention, the method also includes the dissolution of a liquid-soluble membrane, which divides the reaction chamber into a first reservoir chamber and a second reservoir chamber, by the first and second liquids before the mixture of the first and second liquids. The division of the reaction chamber into first and second reaction areas is ended by the dissolution of the membrane, so there is a mixture of the first and second liquids that exist in the first and second reservoir chambers.

The microfluidic, micro-chemomechanical system is used in accordance with the invention for the execution of processes based on antigen-antibody reactions, the execution of processes based on the cultivation method, the control and/or detection of processes based on a polymerase chain reaction and the detection of enzyme activity of a biochemical process. Further applications based on chemical or biochemical mixing reactions are conceivable.

The microfluidic, micro-chemomechanical system as per the invention distinguishes itself by the fact that it makes the mixing of first and second liquids possible in a reaction chamber with a defined volume and in a time-controlled manner without the use of auxiliary energy. Moreover, immobilized active ingredients and/or other substances can be released in a time-controlled manner and make reactions in the reaction chamber possible in that way.

The above-mentioned embodiments in accordance with the invention are suitable for solving the problem. In so doing, combinations of the disclosed embodiments are also suitable for solving the problem. Preferred further design developments of the invention follow from the combinations of claims or individual features thereof.

The invention is to be explained in more detail below with the aid of a few examples and the accompanying figures. The examples are intended to describe the invention without limiting it to them.

DETAILED DESCRIPTION OF THE PREFERRED EMBODIMENTS

Figure 1:
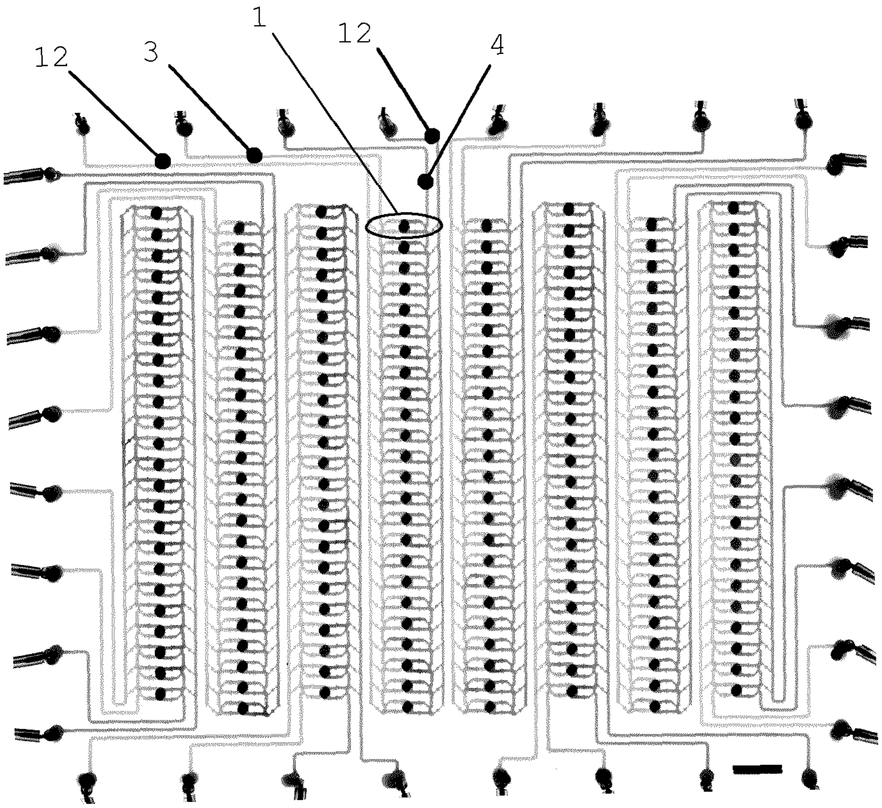
FIG. 1 shows a top view of a microfluidic, micro-chemomechanical system as per the invention.

In a first example, a microfluidic, micro-chemomechanical system as per the invention is shown in FIG. 1 that is conceptually designed in the form of an autonomous and automatic microfluidic processor for equidistant, long-term investigations. The microfluidic processor in FIG. 1 carries out long-term investigations that are comprised of identical analytical reactions or other mixing reactions and that are repeated in accordance with a defined schedule. Equidistant investigations are included among the most useful processes in science and technology. They are used, among other things, for the control of critical parameters, e.g. the monitoring of bioreactors, for enzyme analysis and for the analysis of growth factors or the quality control of chemical and biological products. The microprocessor in FIG. 1 is divided up into 192 serially connected, identically constructed stages 1 and includes a total of 2096 active elements 7 and 384 reservoir chambers 9, 10.

Figure 2A:
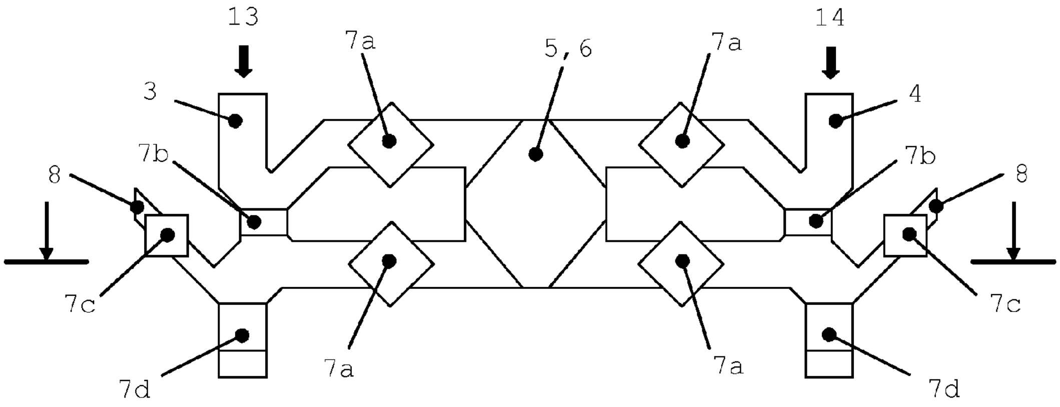
FIG. 2*a* shows a top view of a stage of the micro-chemomechanical system presented in FIG. 1.

In a further example, a stage 1 (FIGS. 2*a*, 2*b*) of the microfluidic processor carries out all of the steps of sampling, sample preparation and initiation of the mixing reaction in a completely independent way and in a self-sufficient way in terms of energy. It does not require any auxiliary electrical energy at all for this and exclusively processes chemical information in the form of a binary concentration c of the process media (c=0: the liquid process medium is not applied; c=1: the liquid process medium is applied). The stage 1 (FIG. 2*a*) operates in the following manner. The liquids 13 and 14 of the two channels 3 and 4 reach the stage 1, so the binary concentration switches over from 0 to 1. This chemical signal activates the integrated active elements 7 and stimulates them to deliver their stored chemical energy in the form of a defined, fluidic function in a sequence of time predefined by the fluidic connection. At first, the liquids flood the components 9, 10 of the reaction chamber 6 in the overlay area 5 of the channels 3 and 4. The closing elements 7*a* consisting, for instance, of the hydrogel sodium acrylate, close the inlets and outlets of the reservoir chambers 9, 10 and thereby separate and measure out the liquids 13, 14. The closing time of the closing elements 7*a* is chosen in such a way that the reservoir chambers 9, 10 are completely filled with the liquids 13, 14 with a very great probability. It could take 45 s, for instance (ratio of the volume $V_{gel}$ of the sodium acrylate actuator to the volume of the reaction chamber 6 VK 1:5.6, also see FIG. 6*c*). After the reservoir chambers 9, 10 are hermetically sealed, the membrane 7*e* (FIG. 2*b*) dissolves the membrane that separates the reservoir chambers 9, 10 and connects 9, 10 to the reaction chamber 6. The desired reaction can now take place via the mixture of the liquids 13, 14. The membrane 7*e*, which is designed to be an active membrane, for instance, has to have enough mechanical stability that it will not be significantly deflected when the reservoir chambers 9, 10 are flooded. Moreover, its dissolution or opening time period is not permitted to be too short to avoid undesired, premature mixing. Appropriate dimensional stability can be realized with an opening time of 7 min. via the use of an active membrane 7*e* made of non-cross-linked polyvinyl alcohol with a thickness of 70 μm, for instance (also see FIG. 7*a*).

The opening elements 7*b* that are made of polyethylene glycol (PEG) 6000, for instance, are closed in the chamber bypasses during the filling of the reservoir chambers 9, 10. The increasing pressure on the opening elements 7*b* leads to a through-hole in them as soon as 9, 10 are closed by the closing elements 7*a*. After that, the elements 7*b* quickly and completely dissolve. The opening elements 7*b* are essential elements for sequential circuits with multiple stages or cascades. Without them, the fluidic resistors of the bypass channels would have to chosen to be much greater than the fluidic resistances of the channels leading to the reservoir chambers. This would cause the number of stages that could be added in series to be limited to 3 or 4 because of the resistances that are added up because of the series connection. Since the opening elements 7*b* completely dissolve, the bypass resistance can be kept low enough that the number of sequential stages virtually has no more limit. The opening element 7*d* defines the time period until the activation of the next stage. The liquids 13, 14 flood the next sages after the opening elements 7*d* dissolve. In that moment, the closing elements 7*c* close the bypasses to the circulation channels 12 evident in FIG. 1. It is also possible in the case of the circuit combination of elements 7*c* and 7*d* to take advantage of the increase in pressure on the opening element 7*d* as a result of the closure of 7*c* to open 7*d*. The microprocessor shown in FIG. 1 is in a position to carry out mixing reactions at time intervals of 2 min. (opening element 7*d* made of polyethylene glycol 6000 and an element length of 400 μm, also see FIG. 7*c*) in an autonomous and automatic fashion, but it can also operate for up to 16 days with an autonomous and automatic execution of mixing reactions at two-hour intervals (opening elements 7*d* made of PEG 35000 and a length of 1.2 mm).

Figure 2B:
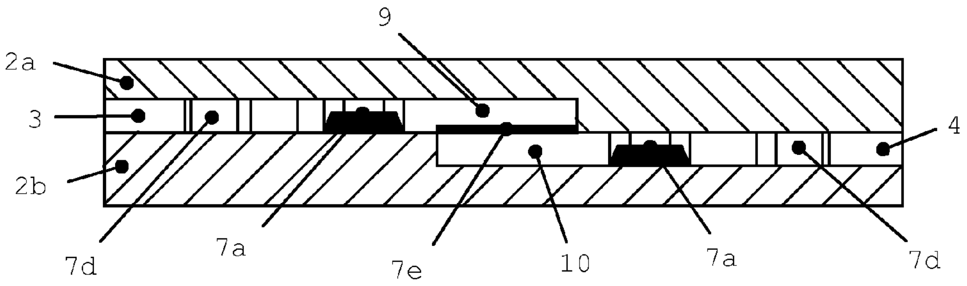
FIG. 2*b* shows a cross-sectional view of the stage presented in FIG. 2*a,*

The microfluidic, micro-chemomechanical system in FIG. 1 has a two-level architecture (see FIG. 2*b*). The upper structure support 2*a*, which acts as a cover, for instance, contains the channel structure of the channel 3 for the liquid 13, whereas the lower channel-structure support 2*b* bears the channel structure of the channel 4 for the liquid 14. Both of the structure supports have a comparable design, for instance, which can basically constitute a mirror image. The channels 3 and 4 are 800 μm wide and 140 μm high for the example shown in FIG. 1. The bypass channels 8 are 400 μm wide and 140 μm high. The square rhombuses for the closing elements have a volume of $1000\times1000\times140\ \mu m^3$ (7*a*) and $800\times800\times140\ \mu m^3$ (7*c*). The configuration of the active elements for the arrangements in FIGS. 1 and 2 is as follows: The thickness of the active membrane made of non-cross-linked polyvinyl alcohol is 70 μm. The length of the opening elements 7*b* (PEG 6000) is 400 μm; the length of the opening elements 7*d* (PEG 6000) is 800 μm. The sodium acrylate actuators of the closing elements 7*a* have a dry volume of $500\times500\times100\ \mu m^3$ (volume ratio $V_{gel}:V_K=1:5.6$), the sodium acrylate actuators of the closing elements 7*c* have a volume of $240\times240\times100\ \mu m^3$ (volume ratio $V_{gel}:V_K=1:16$).

In an alternative design form of the example described above, the microfluidic, micro-chemomechanical system in FIG. 1 is realized with only one structure support 2 and an unstructured cover 2*a*. Both of the channel systems 3, 4 here are on the same structure support 2, i.e. in one plane. An opening element that is structured in principle like the opening elements 7*b*, 7*d* is now arranged between the reservoir chambers 9, 10 in the overlay area of the channels 3, 4; the two reservoir chambers 9, 10 combine to form the reaction chamber 6 after the opening element is dissolved.

In a further example, the monolithic microchips of the microfluidic, micro-chemomechanical systems (FIG. 1) are completely comprised of polymers. The structure supports 2, which contain the channel networks, are comprised of polydimethyl siloxane (PDMS), for instance, and were manufactured with multilayer soft lithography (D. C. Duffy, J. C. McDonald, O. J. A. Schueller, G. M. Whitesides, *Anal. Chem.* 70 (1998), 4974-4984) using a large-area replication technology with masters made of solid resists (A., Richter, G. Paschew, *Adv. Mater.* 21 (2009), 979-983). Multilayer soft lithography using PDMS is primarily suitable for research and demonstrator construction. Other manufacturing processes such as hot-foil stamping and the injection molding of thermoplastic polymers, which could include polystyrene, polycarbonate, olefins such as cycloalkene or polyesters such as polyethylene terephthalate, for instance, are also suitable, above all for the series production of the structure support. Phase-variable polymers that can be integrated into the microchip with simply micro-technical methods are used, as an example, to realize the active element 7. Polyethylene glycols are microstructured via photo lithography with screen printing and sodium acrylate actuators. The active membranes made of polyvinyl alcohol can be integrated with a pick-and-place technology, as an example.

In a further example, the sodium acrylate actuators are microstructured via photo-lithographic polymerization. An exemplary manufacturing procedure is based on a mixture of 2 g of sodium acrylate, 0.04 g of the cross-linking agent N,N'-methylene-bis-acrylamide (BIS) and 0.04 g of the photoinitiator 2-hydroxy-4'-(2-hydroxyethoxy)-2-methylpropriophenone, all of it dissolved in 14 ml of distilled water. This solution is stirred in an argon protective gas atmosphere for 24 hours. This stock solution is referred to as $c_0$ for the discussion in FIGS. 6*a* and 6*b*. The photopolymerization is likewise done in an argon protective gas atmosphere, either directly in the channel structures or in a photopolymerization chamber. The quality and the cross-linking characteristics of the sodium acrylate actuators depend on the polymerization time, the distance to the illumination source, the type of illumination source and the height of the polymerization chamber.

In a further example, meltable polyethylene glycol is used for the opening elements 7*b* and 7*d*, which can be structured with a screen-printing technology. For the example of FIGS. 1 and 2, a structured copper mask with a thickness of 20 μm was placed on the structure supports 2*a*, 2*b* in such a way that their openings were on the target positions of the opening elements 7*b*, 7*d*. The melted PEG is put on the copper mask and distributed with a metal blade in such a way that the opening elements 7*b*, 7*d* in the structure supports 2*a*, 2*b* arise in the mask openings. The PEG cools down and hardens as soon as it makes contact with the structure support. The opening elements that are created already have their geometric dimensions, but they do not yet seal the channels. Hermetically sealed opening valves are achieved in a last microchip-production step by heating the microchip, which has already been completely joined, for a short period of time to slightly over the melting temperature of the PEG. The PEG structures melt and tightly seal the channels.

In a further example, a 5% polymer solution is poured into a mold and subsequently dried to create the active membranes 7*e* made of polyvinyl alcohol. The height of the membrane that is created in this way can be established by the filling quantity and therefore the filling height of the solution in the casting mold.

Figure 3A:
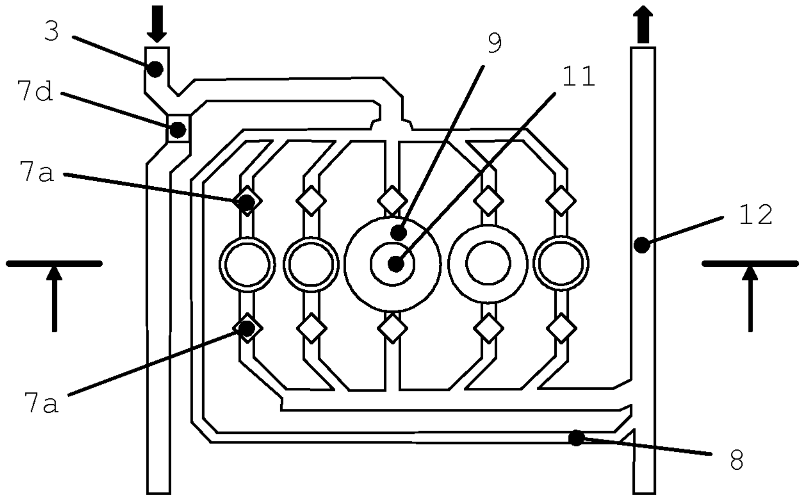
FIG. 3*a* shows a top view of a stage of a further microfluidic, micro-chemomechanical system as per the invention.
Figure 3B:
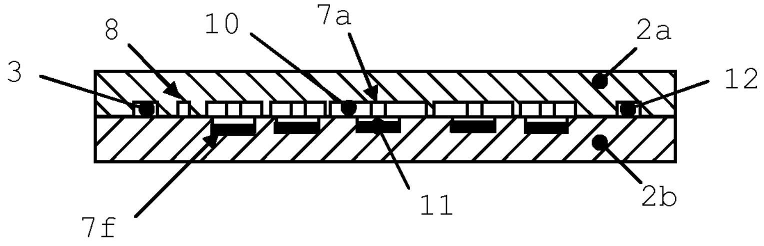
FIG. 3*b* shows a cross-sectional view of the stage presented in FIG. 3*a,*

In a further design example, a microfluidic, micro-chemomechanical system is presented in FIGS. 3*a* and 3*b*. They show the stage of a further microprocessor that is likewise comprised of sequentially connected stages. The stages have the task here of simultaneously carrying out several mixing reactions with different ratios. The simultaneous execution of investigations with various volume ratios of the sample and analyte, or simply two chemicals, makes a determination of reaction kinetics possible, for instance the determination of enzyme activity, among other things.

In a further example, the manner of operation of the stage presented in FIGS. 3*a* and 3*b* is explained with the aid of the investigation of enzyme kinetics. A liquid that contains the enzyme of interest, for instance laccase, a polyphenol oxidase of the mushroom *Trametes versicolor*, is routed through the supply channel 3, which is 800 μm wide and 140 μm high. The medium is forced to flood the five parallel channel structures, which have a width of 400 mm and a height of 140 μm, for instance, with reservoir chambers 9 through the opening element 7*d* that is closed at first. After the reservoir chambers are closed by the closing elements 7*a*, which have dimensions of 700×700×140 $\mu m^3$ for the square valve rhombus, for instance, or dimensions of 300×300×100 $\mu m^3$ for the dry sodium acrylate actuators, at a volume ratio of $V_{gel}:V_K=1:7.6$ for a closing time of 1 min., the process medium first flows over the bypass 8 in the direction of the circulation channel 12 that acts as a drain. This takes place until the opening element 7*d*, which is made of PEG 6000 and which has a length, has opened and the medium in the channel 3 can flow into the subsequent stage. Each of the reaction chambers, which are now hermetically sealed, now contains a volume of process medium containing enzymes that corresponds to the quantity of the reservoir chamber 9. Furthermore, each reservoir chamber 9 has a storage area 11 in the base area where an analyte in the form of a dried, liquid-soluble active element 7*f* has already been brought in during the production of the microchip. The active element 7, containing the analyte, is comprised here of a dried, immobilized substrate 2,2'-azino-bis(3-ethylbenzthiazoline-6-sulphonic acid), for instance, in a malonate buffer. The presence of the aqueous process medium lets the substrate be dissolved, and the mixing reaction starts. The reservoir chambers 9 and the storage areas 11 found in them represent volume ratios of sample to analyte of 1:3, 1:2, 3:1, 2:1 and 1:1, for example.

Figure 4:
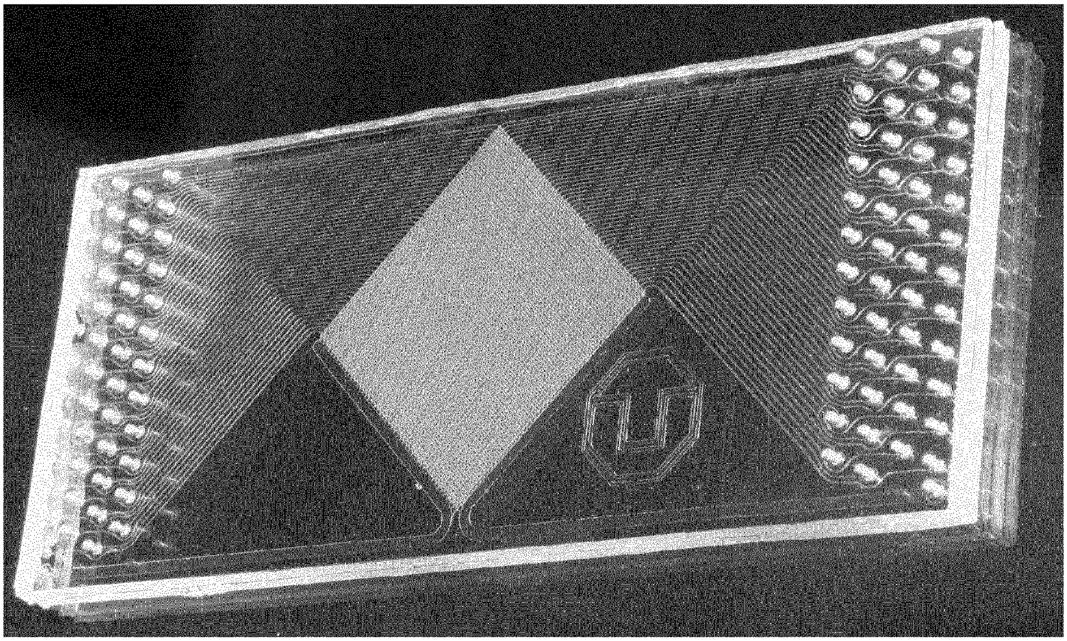
FIG. 4 shows a depiction of a further microfluidic, micro-chemomechanical system as per the invention with a 48×48 mixing matrix.
Figure 5A:
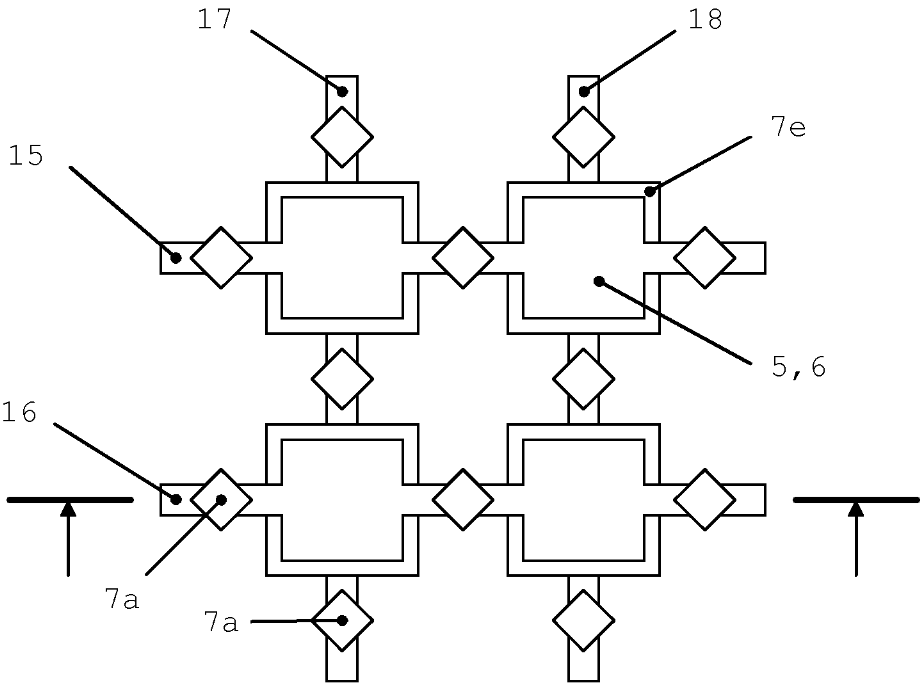
FIG. 5*a* shows a top view of a 2×2 section from the matrix of FIG. 4.
Figure 5B:
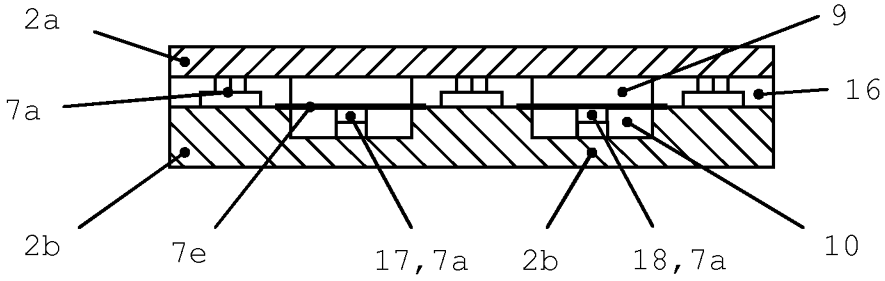
FIG. 5*b* shows a cross-sectional view of a matrix section presented in FIG. 5*a,*

In a further example, a microfluidic, micro-chemomechanical system is introduced in FIG. 4 that realizes all possible combinations of N chemicals organized in rows with M chemicals organized in columns in the form of a highly parallel, microfluidic [N×M] matrix processor operating autonomously and automatically. A [48×48] matrix processor is presented in FIG. 1. An exemplary application scenario of a [48×48] matrix processor is the parallel investigation of 48 samples for 48 parameters, for instance for screening purposes. The advantage of matrix processors of this type is that all of the investigations are carried out at the same point in time under exactly the same conditions. The massive parallel execution of the tests also brings out the advantages of a high level of integration, so investigation series that typically take days or weeks can be carried out in hours. The [48×48] matrix processor carries out 2304 investigations simultaneously and fully automatically. It has a total of 2401 closing elements 7*a* and 2304 active membranes 7*e*. Its manner of operation will be explained below with the aid of FIGS. 5*a* and 5*b* for a [4×4] matrix section and a sample configuration.

Liquids are brought at the same time and with the same flow rate into the row channels 15 and 16 and the column channels 17 and 18; sample liquids, for instance, are brought into the row channels 15 and 16 and analytes, for example, are brought into the column channels 17 and 18.

The liquids of the row channels 15, 16 flood the reservoir chambers 9; the liquids of the column channels 17, 18 simultaneously flood the reservoir chambers 10. The closing elements 7*a* hermetically seal the reservoir chambers after approx. 1 min.; the dimensions of the square valve rhombuses are 700×700×140 $\mu m^3$, and the dimensions of the dry sodium acrylate actuators are 300×300×100 $\mu m^3$ at a volume ratio of $V_{gel}:V_K=1:7.6$. With the dimensioning of the closing valves 7*a*, it must be ensured that they will only close when all of the reservoir chambers have been completely flooded. After the hermetic sealing of the closing elements 7*a*, the active membranes 7*e* dissolve within approx. 3 min., the membranes are designed to be made of polyvinyl alcohol with a thickness of 50 μm, for instance, wherein the 2×2=4 possible mixing reactions take place simultaneously.

Figure 5C:
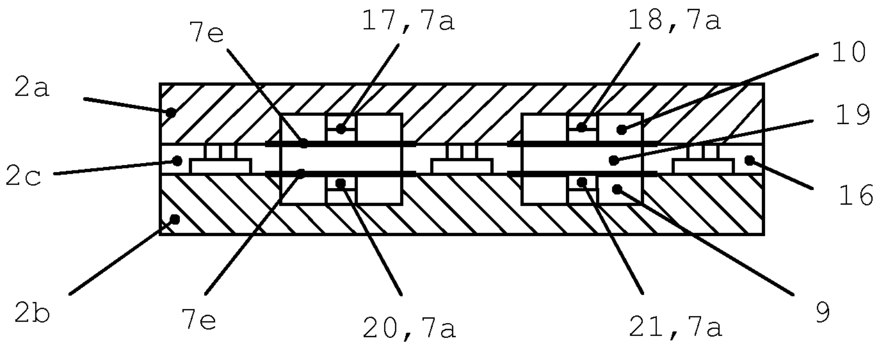
FIG. 5*c* shows a cross-sectional view of an alternative design of a matrix section presented in FIG. 5*a,*

In a further example, FIG. 5*c* illustrates that more than two liquids can be mixed with one another by adding further fluid levels in every matrix point. In the example that is shown, a further intermediary structure support 2*c* is integrated into the overall structure that has a configuration of active elements 7*a*, 7*e* similar to that of the two other structure supports 2*a*, 2*b*. Because of this simple stacking of three structure supports, it is possible to combine three reservoir chambers 9, 10, 19, which are fed by different channels 16, 18, 21, to form a reaction chamber 6 and thus mix three liquids with one another in one matrix point.

Figure 6A:
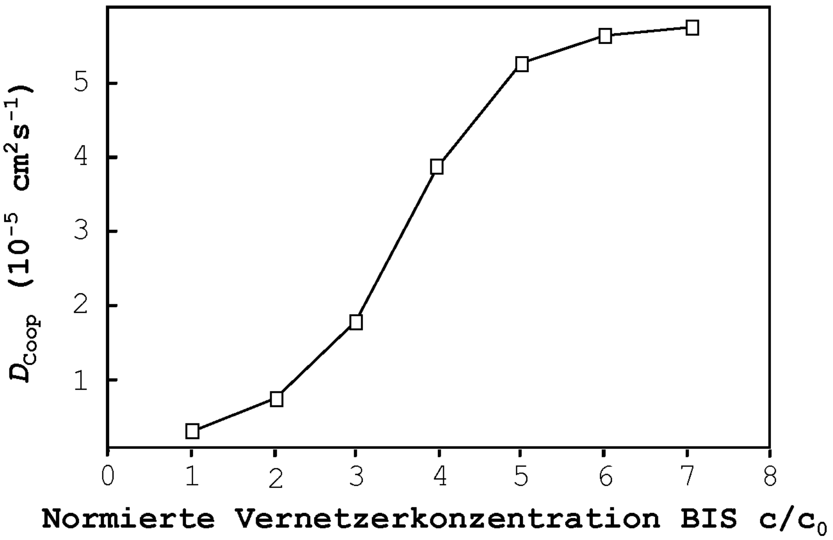
FIG. 6*a* is a diagram that shows the dependence of cooperative diffusion coefficients of swelling-medium barriers based on sodium acrylate hydrogels in dependence upon their standardized cross-linking agent concentration.
Figure 6B:
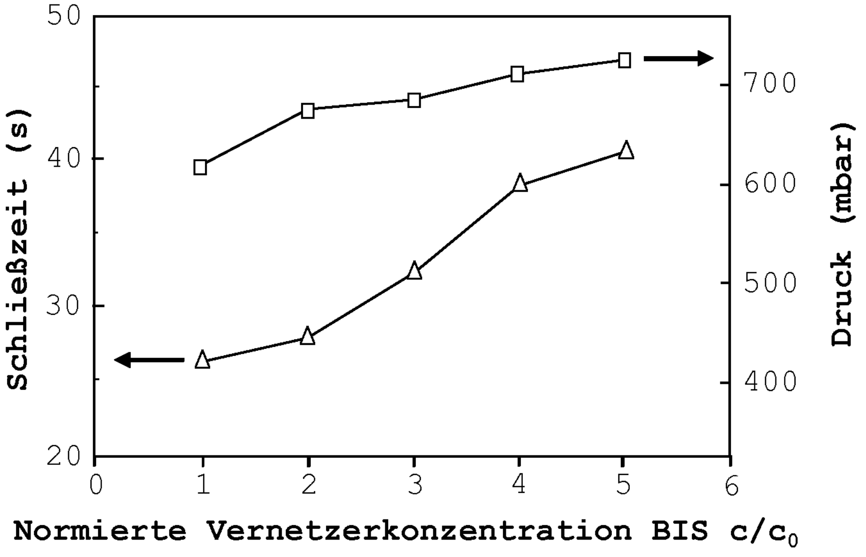
FIG. 6*b* is a diagram that shows the dependencies of the closing time and the pressure resistance of swelling-medium barriers based on sodium acrylate hydrogels in dependence upon their standardized cross-linking agent concentration.
Figure 6C:
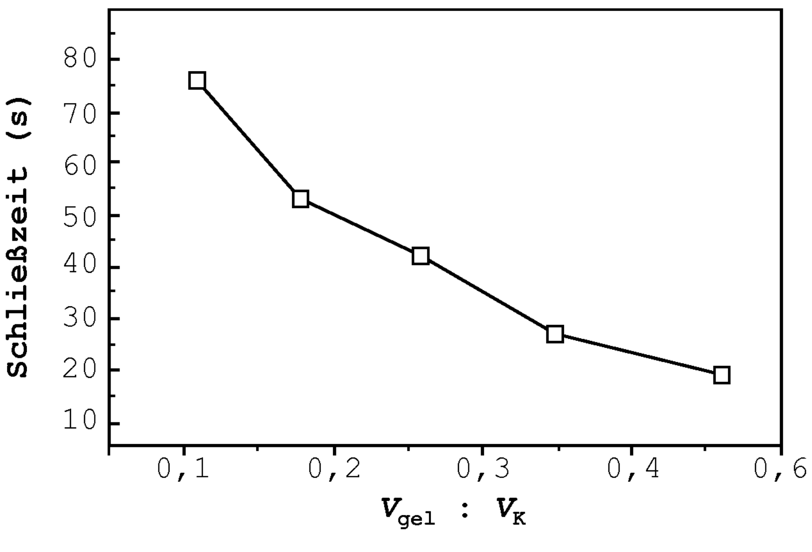
FIG. 6*c* is a diagram that shows the dependencies of the closing time of swelling-medium barriers based on sodium acrylate hydrogels in dependence upon the ratio of the volume of the hydrogel actuator in the dry, starting state to the volume of the valve chamber.

In a further example, FIGS. 6*a*, 6*b* and 6*c* show possibilities for predefining the parameters of the closing elements 7*a*, 7*c*, especially the closing time and the pressure resistance, via a choice of material and design parameters. FIG. 6*a* illustrates that the closing time can be preset by the hydrophilic characteristic or the cooperative diffusion coefficients of the selected material. Two hydrogel types can be distinguished, neutral hydrogels and poly-electrolytic hydrogels. Neutral hydrogels such as interlinked polyacrylamide, poly(N-isopropylacrylamide), polymethylvinyl ether, polyvinyl alcohol or polyethylene glycol have cooperative diffusion coefficients $D_{coop}$ on the order of $10^{-7}$ $cm^2s^{-1}$. These hydrogels are predestined to be the material basis for relatively slow closing elements with closing times in the range of minutes or hours. Poly-electrolytic hydrogels that contain ionizable groups, e.g. acid or base groups, have cooperative diffusion coefficients on the order of $10^{-7}$ to $10^{-5}$ $cm^2s^{-1}$ due to additional intermolecular and intramolecular electrostatic interactions that have an expansionary effect. Poly-electrolytic hydrogels that are used as super-absorbers have the greatest $D_{coop}$. The hydrogel sodium acrylate is among them. As FIG. 6*a* shows, the $D_{coop}$ of sodium acrylate is dependent upon the interlinking conditions. The more the cross-linking agent N,N'-methylene-bis-acrylamide (BIS) is used, the greater the cooperative diffusion coefficient and the quicker the swelling of the hydrogel. The influence of the cross-linking agent content is significantly reduced starting at a standardized concentration of $c/c_0=7$. FIG. 6*b* illustrates that the closing time of a sodium-acrylate closing elements increases with an increasing concentration of the cross-linking agent. That is not in conflict with the statement of FIG. 6*a*. The hydrogel is effectively slower despite a higher Dcoop, because a higher cross-linking agent content leads to a higher cross-linking agent density of the hydrogel. The higher cross-linking agent density leads, on the other hand, to hydrogels with greater mechanical stability, so the pressure resistance of the closing elements increases with an increasing cross-linking agent content or an increasing cross-linking density of the sodium acrylate actuators. Aside from the chemical parameters, the closing time of the closing elements can also be set via a design quantity, namely the ratio of the dry volume of the sodium acrylate hydrogel actuators to the reaction chamber volume of the closing-element seat (FIG. 6*c*).

Figure 7A:
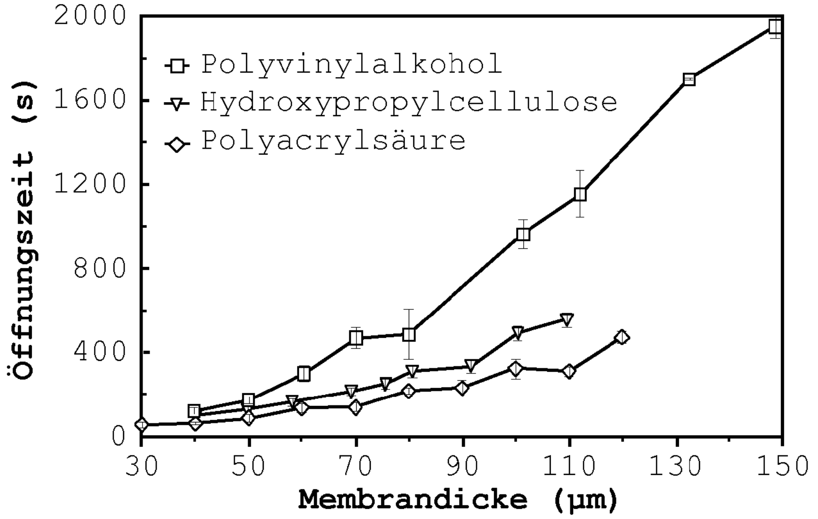
FIG. 7*a* is a diagram that shows the dependence of the opening time of liquid-soluble barriers on the liquid-soluble material that is used and on the thickness of a barrier designed to be a membrane.
Figure 7B:
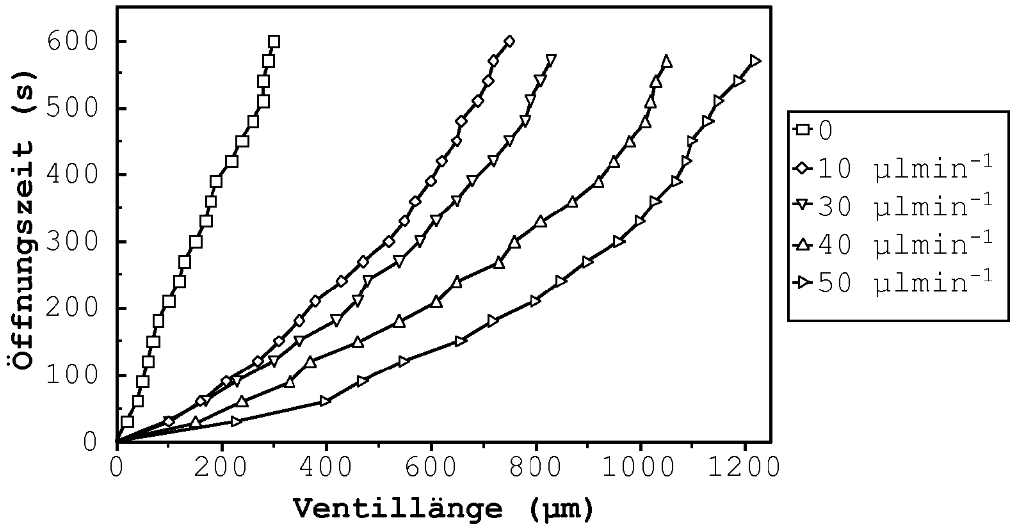
FIG. 7*b* is a diagram that shows the dependence of the opening time of liquid-soluble barriers in the form of an opening valve made of PEG 10.000 on the valve length for various flow velocities of the process medium.
Figure 7C:
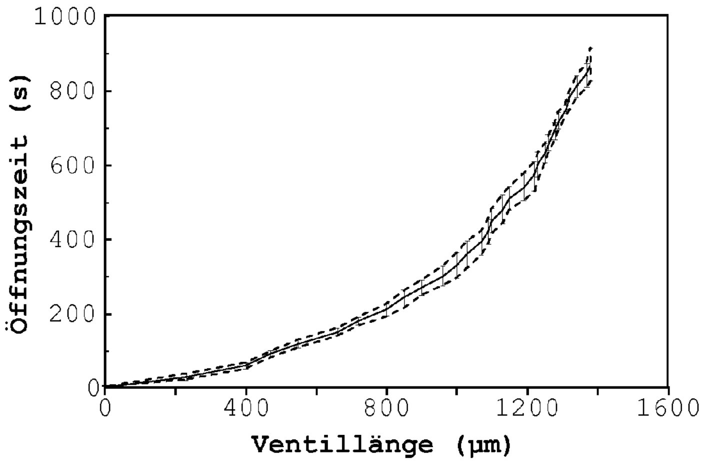
FIG. 7*c* is a diagram that shows the standard deviation of the opening time of liquid-soluble barriers in the form of an opening valve made of PEG 6.000 on the valve length.

The opening times of opening elements 7*b*, 7*d* and 7*e* can likewise be present via the choice of material (FIG. 7*a*). The more hydrophilic the water-soluble polymer that is selected, the quicker the active element dissolves. A design parameter is of major significance for the opening time: the thickness of the active membranes (FIG. 7*a*) or the length of the opening elements (FIG. 7*b*). Polymers with a high glass temperature are suitable for being membranes in an advantageous way. These polymers are mechanically stable, and thin membranes that are resistant to bending can be manufactured. Suitable candidates with glass temperatures that are substantially higher than room temperature are, for example, polyvinyl alcohol ($T_g$=85° C.), hydroxypropyl cellulose ($T_g$=105° C.) and polyacrylic acid ($T_g$=105° C.). Significantly softer materials, e.g. polyethylene glycol, can also be used for the opening elements 7*b* and 7*d* that are not stressed by flexure. In contrast to the closing elements the flow velocity of the liquid flowing past has a significant influence on the opening time of opening elements. As FIG. 7*b* illustrates, opening elements open very slowly when there is a stagnating liquid. In that case, saturation zones made of dissolved polymer that interfere with the further dissolution process of the polymer could form in front of the opening element. These saturation zones are destroyed with an increasing flow velocity, and the polymer dissolves faster. FIG. 6*c* demonstrates, with the example of a PEG 6000 opening element, that the standard deviation of active elements 7 can already be kept very low with simple micro-technical laboratory manufacturing methods.

In a further example that is not shown in more detail, an enzymatic test for determining the content of uric acid is described. The content of uric acid in serum or urine provides information about the breakdown of purine bases and is used when there is a suspicion of gout and for monitoring cell-destroying processes and lithiasis. The recommended upper limit for men is at 416 μmol/l.

The test is carried out in the form of a coupled enzyme test in which uric acid is oxidized by the uricase. In the process, hydrogen peroxide arises that can be detected with a peroxidase (HRP).

$$\text{Uric acid}+O_2+2H_2O\rightarrow\text{allantoin}+CO_2+H_2O_2\text{uricase}$$

$$\text{Substrate}_{red}+H_2O_2\rightarrow\text{Substrate}_{oxd}+H_2O+h^*\nu\ \text{HRP}$$

In the microfluidic chip, the substrate Amplex Red (5 mM in DMSO) is first mixed with the 99-fold volume of an enzyme solution (0.1 M Tris/HDI, pH 7.4; 0.2 U/ml uricase; 0.2 U/ml HRP) and put into a stage 1 of the microfluidic, micro-chemomechanical system. The reaction solution that arises is subsequently brought via the second channel 4 into the second reservoir chamber, whereas the first reservoir chamber 9 is filled with the same volume of the sample to be investigated (containing 0-100 μM uric acid) via the first channel 3. The soluble membrane 7*e*, which separates the reservoir chambers 9, 10 from one another, dissolves as a result of the contact with liquid; the reaction chamber 6 is formed because of that, and the reaction partners are mixed. The enzymatic conversions take place now at a reaction temperature of 37° C. After 5 minutes of reaction time, a fluorescence at 590 nm can be detected after stimulation with light (530 nm). The concentration can be calculated from the intensity of the fluorescence via an appropriate calibration.

In a further example, protein detection with ortho-phthalaldeyde (OPA) is described. The protein is converted with the detection reagent OPA with the participation of a component containing thiol, for instance β-mercaptoethanol. In so doing, a fluorophore arises that can easily be detected.

Ortho-Phthalaldehyde+Protein+β-Mercaptoethanol→Fluorophore

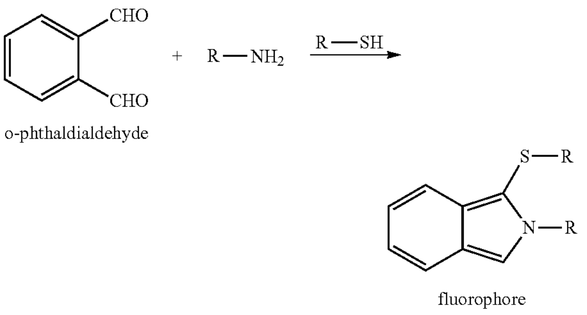

To execute the process in the microfluidic chip, 100 μl of the detection reagent (6 μg/ml OPA; 0.1 M phosphate buffer, pH 7.4; 0.05% by vol. β-mercaptoethanol) is filed in the first reservoir chamber 9, whereas 100 μl of the sample to be investigated, for instance a 5-fold diluted serum, is put into the other reservoir chamber 10. Both of the reservoir chambers 9, 10 have the same volume here. A reaction comes about as soon as the soluble membrane 7*e* between the two reservoir chambers 9, 10 has dissolved as a result of the contact with liquid and the components have been mixed. After 2-3 minutes, the resulting signal can be read out of the reaction chamber 6. Light with a wavelength of 340 nm is radiated in for that, and the fluorescence at 455 nm that is radiated out is detected (J W. Viets, W M. Deen, J L. Troy and B M. Brenner, Analytical Biochemistry 88, 513-521 (1978)). A Microplate Reader Infinite M200 (TECAN Group Ltd., Switzerland) was used for detection.

Figure 8A:
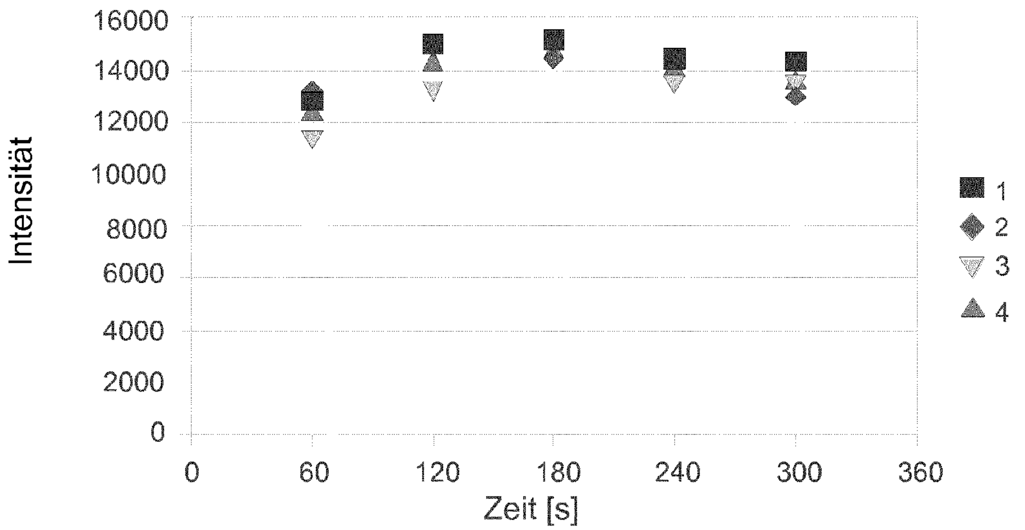
FIG. 8*a* shows the course of the fluorescence intensity of four different protein samples at 455 nm after mixture with a detection reagent over time.
Figure 8B:
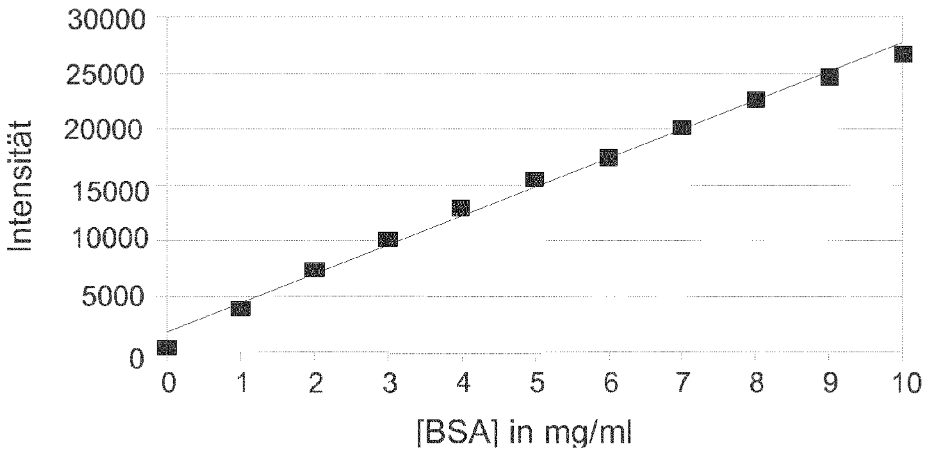
FIG. 8*b* shows a calibration line for determining the protein concentration in a sample.

FIGS. 8*a* and 8*b* show the time-dependent course of the detected fluorescence intensity of four samples at a wavelength of 455 nm. The corresponding protein concentration (FIG. 8*a*) can be determined from a calibration line (FIG. 8*b*) based on BSA as the reference protein.

Figure 9A:
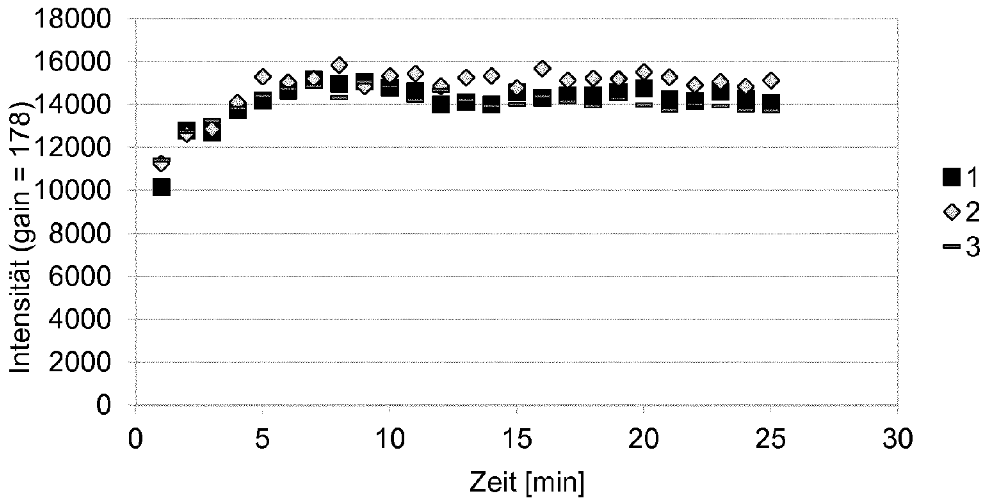
FIG. 9*a* shows the fluorescence intensity in the case of the detection of human serum albumin (HSA) as a triple identification at 423 nm after mixture with a detection reagent over time.
Figure 9B:
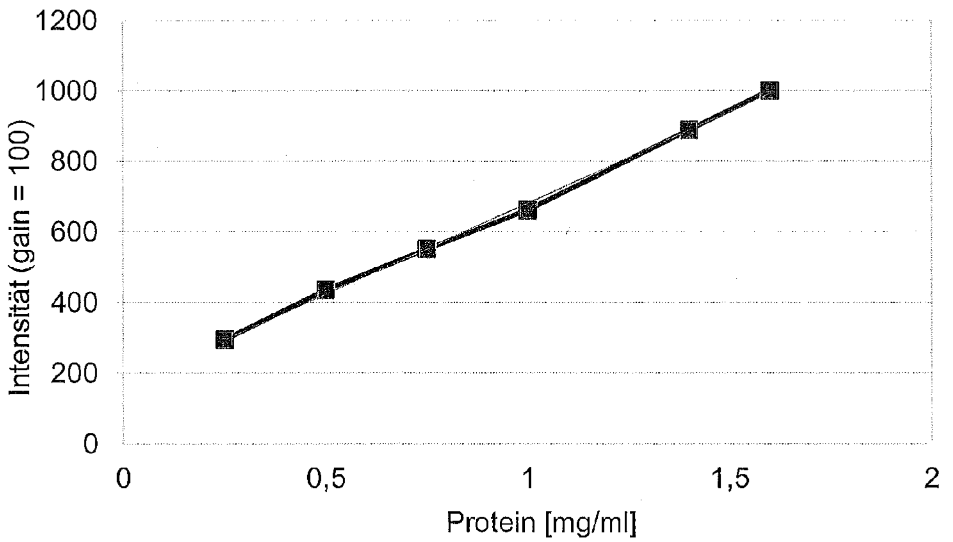
FIG. 9*b* shows a calibration line for determination of the protein concentration of human serum albumin (HSA) in a sample.

The detection of myoglobin in blood is described in one example (FIGS. 9*a* and 9*b*). Antibodies are immobilized in the reaction chamber 6 in the process. After that, the sample is put into the reaction chamber 6 that is coated with an antibody (anti-myoglobin) and incubated for 1 hour at RT (room temperature). Washing is subsequently done with a washing solution (137 mM sodium chloride, 2.7 mM potassium chloride, 12 mM phosphate buffer, pH 7.4, 0.05% Tween 20). After that, the antibody solution (anti-myoglobin-HRP or anti-myoglobin-GFP) is added and incubated for 1 hour at RT. Washing subsequently done once again with the washing solution. Finally, the signal can be directly read out (GFP 475/530 nm) or the reaction solution (0.1 M Tris/HCl, pH 7.5; 10 μM $H_2O_2$, 50 μM Amplex Red) has to now be added to read out the signal that arises (Amplex Red Ex: 530 nm Em: 590 nm). The washing solution can be supplied via the first or second channel 3, 4 in the process.

To carry out the detection of human serum albumin (HSA) in the microfluidic chip, 100 μl of the detection reagent (2 μM ECR solution 0.02% (m/v) PVA; 20 mM sodium acetate buffer, pH 4.6) is filled in the first reservoir chamber 9, whereas 100 μl of the serum sample to be investigated (diluted 1:100) is routed into the other reservoir chamber 10. Both of the reservoir chambers 9, 10 have the same volume here. A reaction comes about as soon as the soluble membrane 7*e* between the two reservoir chambers 9, 10 has dissolved as a result of the contact with liquid and the components have been mixed. After incubation of 10 minutes, the resulting signal can be read out of the reaction chamber 6. Light with a wavelength of 308 nm is radiated in for that, and the fluorescence radiated out at 423 nm is detected (Yun-Xiang Ci* and Lie Chen, Analyst (1988), vol. 113, p. 679). A Microplate Reader Infinite M200 (TECAN Group Ltd., Switzerland) was used for detection.

FIG. 9*a* shows the time-dependent course of the detected fluorescence intensity of a triple identification of a HSA sample (0.3 mg/ml) at a wavelength of 423 nm. The reaction reached a stable intensity maximum at approx. 1500 after approx. 15 minutes. The corresponding protein concentration can be determined in the process from a calibration line based on BSA as the reference protein. FIG. 9*a* shows the fluorescence intensity that is determined in the case of the detection of HSA as a triple identification at 423 nm after mixture with a detection reagent over time (gain: 178). The corresponding protein concentration of the sample can be determined via a calibration line (FIG. 9*b*) (gain: 100).

In a further example of the invention, the protein verification is described with the example of bovine serum albumin (BSA) with fluorescamine.

Fluorescamine reacts with amino acids to form pyrolinone derivatives that can be stimulated at a wavelength of 395 nm; a fluorescence maximum can be detected at 470 nm.

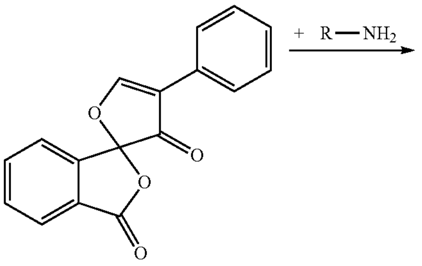

Fluorescamine
(colorless)

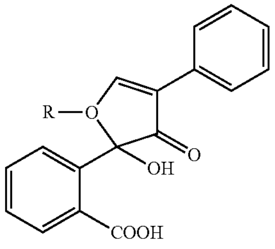

Fluorescamine adduct
(strongly fluorescent)

To carry out the protein detection with fluorescamine in the microfluidic chip, 40 μl of fluorescamine in DMSO in 100 μl of a boric acid buffer (0.05 M, pH 9.5) is filled in the first reservoir chamber 9, whereas 10 μl of the serum sample to be investigated (diluted 1:100) is routed into the other reservoir chamber 10. Both of the reservoir chambers 9, 10 have a different volume here. A reaction comes about as soon as the soluble membrane 7*e* between the two reservoir chambers 9, 10 has dissolved as a result of the contact with liquid and the components have been mixed. After incubation of 2 to 3 minutes, the signal can be read out of the reaction chamber 6. Light with a wavelength of 395 nm is radiated in for this, and the fluorescence at 470 nm that is radiated out is detected. A Microplate Reader Infinite M200 (TECAN Group Ltd., Switzerland) was used for detection.

Figure 10:
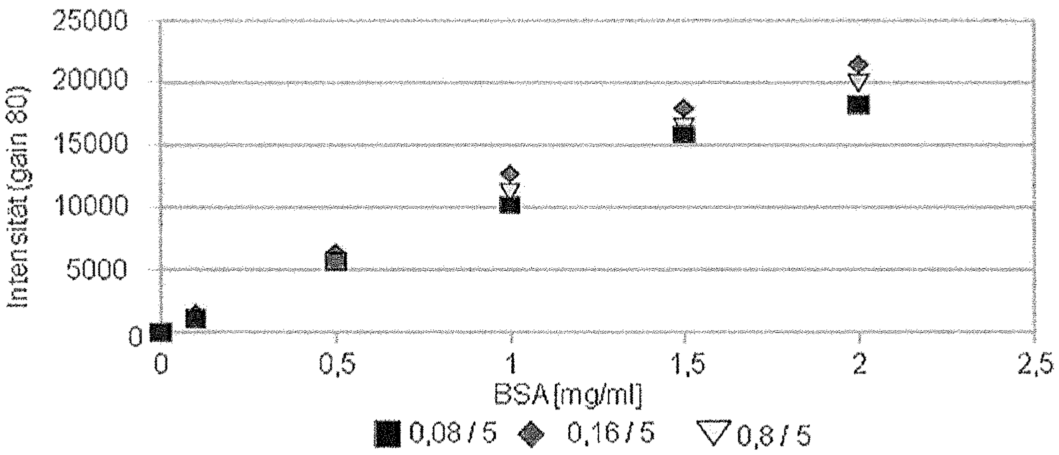
FIG. 10 shows the concentration-dependent fluorescence intensity that was determined in the case of the detection of bovine serum albumin (BSA) as a triple identification at 470 nm after mixture with fluorescamine.

FIG. 10 shows the concentration-dependent fluorescence intensity that was determined from a triple identification of a BSA sample at a stimulation wavelength of 395 nm. The fluorescence intensity increases with an increasing concentration of BSA. The bovine serum albumin (BSA) is detected in the process in the form of a triple identification at 470 nm after mixture with fluorescamine (gain: 80).

LIST OF REFERENCE NUMERALS

1 Stage of a microfluidic, micro-chemomechanical system
2 Structure support
2*a* Cover/upper structure support
2*b* Lower structure support
2*c* Intermediate structure support
3 First channel
4 Second channel
5 Overlay area
6 Reaction chamber
7 Active element
7*a* Closing element
7*b* Opening element
7*c* Closing element
7*d* Opening element
7*e* Active membrane
7*f* Active element delivering active ingredients or other substances
8 Bypass
9 First reservoir chamber
10 Second reservoir chamber
11 Storage area
12 Circulation channel
13 First liquid
14 Second liquid
15 Row channel 1
16 Row channel 2
17 Column channel 1
18 Column channel 2
19 Third reservoir chamber
20 Column channel 3
21 Column channel 4

The invention claimed is:

1. Microfluidic, micro-chemomechanical system with integrated active elements (7) that can be activated and increased and decreased in size via influenceable environmental variables without the use of auxiliary energy and that bring about active functions via a change in their swelling state or their mechanical characteristics, said active functions determining a time-related sequence and time-related behavior of liquids in the system, comprising at least one structure support (2) with at least one first channel (3), a cover (2*a*) that at least partially covers the structure support (2), and at least one second channel (4), wherein the second channel (4) is arranged on the structure support (2) or the cover (2*a*), wherein the channels (3, 4) form reservoir chambers (9, 10, 19) limited by active elements (7) in each case, said reservoir chambers being arranged in such a way that they have at least one overlay area (5) vis-a-vis one another and together form a reaction chamber (6), and wherein the size increases and decreases of the active elements fully or partially block and unblock the channels and are controlled by the dimensions and materials of the active elements.

2. Microfluidic, micro-mechanical system according to claim 1, characterized in that a membrane (7*e*) is arranged between the first and second channels (3, 4) in an overlay area (5) of the first and second channels (3, 4) causing the reaction chamber (6) to be divided up into a first reservoir chamber (9) and a second reservoir chamber (10).

3. Microfluidic, micro-mechanical system according to claim 1, characterized in that further channels (16, 18, 21) are provided, wherein membranes (7*e*) are arranged between the reservoir chambers (9, 10, 19) belonging to the channels (16, 18, 21), said reservoir chambers forming the reaction chamber (6), in the overlay areas (5) of more than two channels (16, 18, 21).

4. Microfluidic, micro-mechanical system according to claim 1, characterized in that an opening element (7*b*, 7*d*) is arranged between the first and second channels (3, 4) in the overlay area (5) of the first and second channels (3, 4) causing the reaction chamber (6) to be divided up into a first reservoir chamber (9) and a second reservoir chamber (10).

5. Microfluidic, micro-mechanical system according to claim 1, characterized in that the membranes (7*e*) or the opening elements (7*b*, 7*d*) are between the first, second and possibly further reservoir chambers (9, 10, 19) made of a liquid-soluble material.

6. Microfluidic, micro-mechanical system according to claim 1, characterized in that the reaction chamber (6) is comprised of at least one first reservoir chamber (9) and one second reservoir chamber acting as a storage area (11), wherein an active element (7*f*) is arranged in the storage area (11).

7. Microfluidic, micro-mechanical system according to claim 6, characterized in that the active element (7*f*) in the base area of the storage area (11) is a delivery system for active ingredients and/or other substances.

8. Microfluidic, micro-mechanical system according to claim 1, characterized in that the active elements (7) are capable of activation by the presence of liquid as an environmental variable.

9. Microfluidic, micro-mechanical system according to claim 1, characterized in that the active elements (7) are swelling-medium barriers or liquid-soluble barriers.

10. Microfluidic, micro-mechanical system according to claim 1, characterized in that the active elements (7) are made of hydrogels that are chemically cross-linked and/or physically interlaceable.

11. Microfluidic, micro-mechanical system according to claim 10, characterized in that the active elements (7) are made of hydrogels that are selected from a group of cross-linked polymers preferably consisting of polyacrylamides, polyvinyl alcohols, polyacrylates, hydroxycellulose, polyvinyl pyridines or polyglycols such as polyethylene glycol, polypropylene glycol and their derivatives.

12. Microfluidic, micro-mechanical system according to claim 1, characterized in that the active elements (7) are made of non-cross-linked polymers, salts or natural organic substances such as saccharides.

* * * * *